United States Patent
Fujiwara et al.

(10) Patent No.: US 7,166,762 B2
(45) Date of Patent: Jan. 23, 2007

(54) METHOD OF CONSTRUCTING HEART FAILURE MODEL ANIMAL

(75) Inventors: Shuji Fujiwara, Kawachinagano (JP); Shota Ikeda, Ikeda (JP); Keiji Kusumoto, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 214 days.

(21) Appl. No.: 10/380,920

(22) PCT Filed: Sep. 27, 2001

(86) PCT No.: PCT/JP01/08418

§ 371 (c)(1),
(2), (4) Date: Mar. 18, 2003

(87) PCT Pub. No.: WO02/26031

PCT Pub. Date: Apr. 4, 2002

(65) Prior Publication Data

US 2004/0006781 A1    Jan. 8, 2004

(30) Foreign Application Priority Data

Sep. 27, 2000  (JP) ............................. 2000-294988

(51) Int. Cl.
*A01K 67/00*  (2006.01)
*G01N 33/00*  (2006.01)
(52) U.S. Cl. .............................................. 800/9; 800/3
(58) Field of Classification Search ................... 800/9, 800/3
See application file for complete search history.

(56) References Cited

OTHER PUBLICATIONS

Meggs LG, Coronary artery stenosis in rats affects beta-adrenergic receptor signalling in myocytes, 1997, Cardiovascular Res. vol. 33, pp. 98-109.*

Anthonio RL, Myocardial infarction and aortic banding, 1997, Japan Heart Journal, vol. 38, pp. 697-708.*

Bing OH, Studies of prevention, treatment and mechanisms of heart failure in the aging spontaneously hypertensive rat, 2002, vol. 7, pp. 71-88.*

Galinanes M, Impaired Cardioplegic Delivery and the Loss of Cardioprotection: a Role for Preconditioning, 1997, J. Mol. Cell Cardiol., vol. 29, pp. 849-854.*

J.M. Power, et al., "Large Animal Models of Heart Failure", Australian and New Zealand Journal of Medicine, (1999), pp. 395-402, vol. 29, No. 3, XP008030977.

K. Hashimoto, et al., "Positive Inotropic Effect of 3,4-Dihydro-6-[4-(3,4-dimethoxybenzoyl)-1-piperazinyl]-2(1H)-quinolinone (OPC-8212) in the Dog with Experimentally-induced Right-sided Heart Failure", Arzneimittel-Forschung/Drug Research, (1984), pp. 390-393, 34/3, XP008039188, Figure 1.

K. Kusumoto, et al., "In vitro and in vivo Pharmacology of a Non-acylguanidine Na-H Exchange Inhibitor, T-162559", Journal of Molecular and Cellular Cardiology, (2001), pp. A64, vol. 33, No. 6, XP002306982—abstract.

Anthonio, et al. "Myocardial Infarction with Aortic Banding A Combined Rat Model of Heart Failure" University of Groningen, The Netherlands. pp. 697-7088 (Feb. 26, 1997k).

Turcano, et al. "Minoxidil accelerates heart failure development in rats with ascending aortic constriction" Can. J. Physiol. Pharmacol 76: 613-620 (1998)).

Linz, et al. "Ace Inhibition Decreases Postoperative Mortality in Rats with Left Ventricular Hypertrophy and Myocardial Infarction" Clin. and Exper. Hypertension 18(5) :691-712 (1996).

Nolan, et al. "Increased Afterload Aggravates Infarct Expansion After Acute Myocardial Infarction" JACC 12(5): 1318-1325 (Nov. 1988).

Takechi, et al. "Recovery of Cardiac Norepinephrine Concentration and Tyrosine Hydroxylase Activity by the Central $\alpha_2$-Adrenoceptor Agonist Guanabenz in Rats with Aortic Constriction" Journal of Cardiovascular Pharmacology 33:409-413 (1999).

* cited by examiner

*Primary Examiner*—Dave Trong Nguyen
*Assistant Examiner*—David A. Montanari
(74) *Attorney, Agent, or Firm*—Elaine M. Ramesh; Mark Chao

(57) ABSTRACT

A non-human mammal which is usefully and effectively applicable to the screening of a substance to be employed for preventing and treating heart failure. This animal is an animal model of heart failure prepared by starting both coronary stenosis and the stenosis of arteries other than the coronary artery and the abdominal artery of a non-human mammal within the same period of time.

18 Claims, No Drawings

METHOD OF CONSTRUCTING HEART FAILURE MODEL ANIMAL

This application is the National Phase filing of International Patent Application No. PCT/JP01/08418, filed Sep. 27, 2001.

TECHNICAL FIELD

The present invention relates to an animal model of heart failure and a method of preparation and use thereof.

BACKGROUND ART

The "heart failure" is a generic designation of syndromes, which occur due to the inability of the heart of ejecting blood in an amount required by the organs, and is a disease having the five year survival rate of about 50% and extremely bad prognosis. Nowadays, diuretic agents, digitalis, catecholamine, angiotensine converting enzyme inhibitors, β blocking agents and the like are used for the treatment of heart failure. However, no treatment, except for heart transplantation, can completely suppress the advance of the pathology, or repair the body into a complete healthy body. Therefore, a novel and more useful medicament for the treatment of heart failure has been desired.

In order to find a novel medicament for the treatment of heart failure, a screening using an animal model of heart failure is of importance, and in paticular, an animal model which shows the pathology of the terminal heart failure in a short period and is available for evaluation of the effect on the vital prognosis (survival rate), is highly useful. At present, a rat model in which the coronary artery is ligated permanently (a coronary artery-ligated model) is generally used as a model of heart failure based on myocardial ischemia. However, this model requires a long time to advance to the pathology of the terminal heart failure, and generally requires a test period of a half year to one year for evaluation on the survival rate.

By ligating another artery to add a new load to a coronary artery-ligated model in which only the coronary artery has been constricted, the advancement of the pathology of heart failure may be accelerated. In fact, as a method to prepare an animal model of heart failure by constricting of two or more arteries, for example, Clin. Exper. Hypertension, 18, 691–712 (1996), Linz et al., discloses a method comprising starting stenosis of the abdominal artery 2 weeks before the coronary stenosis. However, in order to achieve the mortality rate of 68%, this method requires a period of 6 weeks after starting the coronary stenosis. Furthermore, J. Am. Coll. Cardiol., 12, 1318–1325 (1988), Nolan et al., discloses a method comprising starting stenosis of the proximal portion of the aorta 3 weeks before coronary stenosis. However, according to this method, the mortality rate after 1 week of the starting of the coronary stenosis is 13%, which shows no difference in comparison with the case that does not accompany stenosis of the aorta. Moreover, as a method to prepare an animal model of heart failure by simultaneously constricting two or more arteries, for example, Jap. Heart J., 38, 697–708 (1997), Anthonio et al., discloses a method comprising simultaneously starting coronary stenosis and the stenosis of the abdominal artery. However, this method requires a period of 6 to 8 weeks to prepare the pathology of heart failure.

PROBLEM TO BE SOLVED BY THE INVENTION

For the screening of a novel medicament for the treatment of heart failure, to construct a useful and effective in vivo evaluation system is an important issue. At present, an animal model of heart failure, which model expresses the pathology of the terminal heart failure in a short period (specifically approximately 1 week), has not been established.

SUMMARY OF THE INVENTION

The present inventors have conducted intensive studies in order to solve the above-mentioned problem, and found that an animal model of heart failure, which model can express the pathology of the terminal heart failure in a short period, can be constructed by simultaneously starting both coronary stenosis and the stenosis of the proximal portion of the aorta in a rat. Furthermore, the present inventors have conducted further studies on that finding, which resulted in the completion of the present invention.

Namely, the present invention relates to:

(1) A method for preparing an animal model of heart failure which comprises starting both coronary stenosis and the stenosis of an artery other than the coronary artery and the abdominal artery in a non-human mammal within the same period of time;

(2) The method according to the above (1), wherein the non-human mammal is a rabbit, a dog, a cat, a guinea pig, a hamster, a mouse or a rat;

(3) The method according to the above (1), wherein the non-human mammal is a rat;

(4) The method according to the above (1), wherein the heart failure state is the decrease of cardiac contractility;

(5) The method according to the above (1), wherein the heart failure state is the increase in the left ventricular end-diastolic pressure;

(6) The method according to the above (1), wherein the heart failure state is cardiac hypertrophy;

(7) The method according to the above (1), wherein the heart failure state is the decrease in reactivity to catecholamine;

(8) The method according to the above (1), wherein the artery other than the coronary artery and the abdominal artery is an aorta;

(9) The method according to the above (8), wherein the aorta is a thoracic aorta;

(10) The method according to the above (1) which comprises starting both coronary stenosis and the stenosis of the proximal portion of the aorta in the non-human mammal within the same period of time;

(11) The method according to the above (1), wherein the coronary stenosis is the blocking of not less than 80% of the blood vessel diameter of the coronary artery;

(12) The method according to the above (1), wherein the stenosis of the artery other than the coronary artery and the abdominal artery is the blocking of 20% to 70% of the diameter of the blood vessel in the artery;

(13) The method according to the above (1), wherein, after the starting of one stenosis, the other stenosis is started while the mammal is still in the acute state due to the former stenosis;

(14) The method according to the above (1), wherein, after the starting of one stenosis, the other stenosis is started within 1 week;

(15) The method according to the above (1), wherein, after the starting of one stenosis, the other stenosis is started within 1 or 2 days;

(16) The method according to the above (1), wherein, after the starting of one stenosis, the other stenosis is started within 60 minutes;

(17) The method according to the above (1), wherein, after the starting of one stenosis, the other stenosis is started within 5 minutes;

(18) The method according to the above (1), wherein the coronary stenosis and the stenosis of the artery other than the coronary artery and the abdominal artery are simultaneously started;

(19) The method according to the above (1), wherein the coronary stenosis and the stenosis at the proximal portion of the aorta are simultaneously started;

(20) The method according to the above (1), wherein the coronary stenosis is started prior to the starting of the stenosis of the artery other than the coronary artery and the abdominal artery;

(21) The method according to the above (1), wherein the survival rate of the animal model of heart failure is not less than 90% after 2 hours of the starting of the stenosis, and the mortality rate of the animal model of heart failure is not less than 20% (preferably not less than 30%, more preferably not less than 40%) after 1 week of the starting of the stenosis;

(22) The method according to the above (21), wherein the mortality rate is not less than 50% after 1 week of the starting of the stenosis;

(23) A method for screening a medical substance which comprises applying a subject substance to the animal model of heart failure according to the above (1), and assaying the effect of the substance on heart failure;

(24) The method according to the above (23), wherein the medical substance is a substance to be used for prevention or treatment of heart failure;

(25) A pharmaceutical composition which comprises a medical substance which has been determined to have the effect on heart failure by the method according to the above (23);

(26) The composition according to the above (25), which is a pharmaceutical composition to be used for prevention or treatment of heart failure;

(27) Use of the animal model of heart failure according to the above (1) for screening of a substance to be used for prevention or treatment of heart failure;

(28) An animal model of heart failure obtainable by the method according to the above (1);

(29) A non-human mammal, wherein both coronary stenosis and the stenosis of artery other than the coronary artery and the abdominal artery have been started within the same period of time; and the like.

DETAILED DESCRIPTION OF THE INVENTION

The "non-human mammal", which may be an objective of the present invention includes simian, cattle, swine, ovine, goat, rabbit, dog, cat, guinea pig, hamster, rat, mouse, and the like. Rabbit, dog, cat, guinea pig, hamster, mouse and rat are preferred, and among these, Rodentia is preferred. Rat (Wistar, S.D. and the like), specifically Wistar rat is the most preferred objective animal for a model animal. The weekold, body weight and the like of the "non-human mammal" as used in the present invention are not specifically limited so long as the mammal is can be applied to the objective screening, however, the modification, for example, increasing or decreasing the mortality rate after 1 week of the starting of the stenosis by suitably modifying these conditions is also possible. Furthermore, a normal animal (an animal which does not express pathology) may be used as the "non-human mammal" used for the present invention, while an animal which expresses pathology such as hypertension, diabetes, obesity, hyperlipidemia, gastric ulcer and the like (for example, spontaneously hypertensive rat (SHR) and the like) may be used for the above-mentioned artery stenosis. When the animal which shows such pathology is subjected to the above-mentioned artery stenosis, the obtained heart failure model animal can supervene, for example, the above-mentioned pathology (e.g., cardiovascular disease such as hypertension, etc., and the like), and such animal can be effectively applied to a screening of a medical substance to be used for prevention or treatment of such complication, or the animal can be applied for a screening of a medical substance, which is effective for only the above-mentioned pathology (e.g., peptic disease such as gastric ulcer, etc., and the like) and does not affect heart failure (which does not aggravate the cardiac dysfunction), or the animal can be applied to a screening, which aims at excluding the subject material that aggravates heart failure from the medical substance to be selected.

Furthermore, not only can the animal model of heart failure in the present invention be effectively applied to the screening of a medical substance to be used for prevention or treatment of heart failure by applying the subject material to determine the improving effect for heart failure, but also can be effectively applied to the screening of various medical substances by applying the subject material to evaluate the effect on heart failure (including aggravated, not affected, improved). Thus, the model animal can be effectively applied aiming at excluding the subject substance that aggravates heart failure from the medical substance to be selected; selecting a subject substance that does not affect heart failure as a medical substance for prevention or treatment of diseases except heart failure; selecting a subject substance, which expresses an improving effect on heart failure, as a medical substance to be used for prevention or treatment of heart failure or the complication of heart failure and a certain disease (e.g., cardiovascular disease such as hypertension, etc., and the like); and the like. Since the animal model of heart failure in the present invention expresses pathology of the terminal heart failure in a short period (specifically, approximately 1 week) and shows a high mortality rate, effects of the subject substances on survival and heart failure (including aggravated, not affected, improved) can be effectively confirmed in a short period. Therefore, this animal model can be applied as a useful model animal in any case of the screening of various medical substances, for any of the above-mentioned purposes.

The "animal model of heart failure" in the present invention is prepared by starting both coronary stenosis and the stenosis of the artery other than the coronary artery and the abdominal artery within the same period of time. Such animal model of heart failure is characterized in that, the survival rate after 2 hours (the individuals that did not recover spontaneous respiration after the above-mentioned artery stenosis (thoracotomy and close-chest operation accompanied with the above-mentioned stenosis of the arteries)) of the starting of the stenosis (wherein the "starting of stenosis" means starting of both coronary stenosis and the stenosis of the artery other than the coronary artery and the abdominal artery, and for example, when the coronary stenosis and the stenosis of the artery other than the coronary artery and the abdominal artery are started at a time interval, the term means the later stenosis among the coronary stenosis and the stenosis of the artery other than the coronary artery and the abdominal artery stenosis) is not less than 90%, and the mortality rate 1 week of starting of the stenosis is not less than 20% (preferably not less than 30%, more preferably not less than 40%), and preferably, the survival rate 2 hours after starting of the stenosis is not less than 95% and the mortality rate after 1 week of starting of the stenosis is not less than 50%. Furthermore, the index of the mortality rate can be set as a mortality rate after 2 to 3 weeks of the starting of the stenosis (40% to not less than 50%), preferably it is set as a mortality rate after 1 week of the starting of the stenosis, more preferably, as a mortality rate after 1 week of starting of the stenosis, and is 40% to not less than 50% (preferably not less than 50%).

The "animal model of heart failure" in the present invention preferably expresses severe cardiac dysfunction within 1 week after the above-mentioned stenosis of the artery. The cardiac dysfunction as used herein includes, for example, an increase in left ventricular end-diastolic pressure, cardiac hypertrophy, hyporeactivity for catecholamine, decrease in cardiac contractility, induction of expression and activation of GRK2 (G protein-coupled receptor kinase), and the like.

The "increase in the left ventricular end-diastolic pressure" as the state of severe heart failure is, for example, in case of a rat, preferably an increase by about not less than 5 mmHg, more preferably an increase by about not less than 10 mmHg, specifically preferably an increase by about not less than 15 mmHg.

The "cardiac hypertrophy" as the state of severe heart failure includes, for example, an increase in the weight of the left ventricle and/or right ventricle and the like, and the increase of the weight of the left ventricle is, for example, in case of a rat, preferably about not less than 200 mg, more preferably about not less than 210 mg per 100 g of the body weight. The increase in the weight of the right ventricle is, for example, in case of a rat, preferably about not less than 50 mg, more preferably about not less than 60 mg per 100 g of the body weight.

The "decrease in the cardiac contractility" as the state of severe heart failure has, for example, in case of rat, preferably not more than about 10000 mmHg/sec, more preferably not more than about 8000 mmHg/sec of the maximum differential value of the internal pressure of the left ventricle. It is desired that the above-mentioned parameters with respect to the cardiac dysfunction show a statistically significant difference in comparison with that of a sham-operated group (an animal group in which the thoracotomy same as that of the artery-constricted group has been conducted but the stenosis of the artery has not been conducted).

The "animal model of heart failure" in the present invention is prepared by starting both coronary stenosis and stenosis of the artery other than the coronary artery and the abdominal artery in a non-human mammal within the same period of time.

As used herein, the artery other than the coronary artery and the abdominal artery includes, for example, intestinal artery, thoracic aorta and the like, preferably aorta such as thoracic aorta and the like. Among these, aorta in the portion more closer to the heart than the abdominal artery (for example, thoracic aorta such as ascending aorta, proximal portion of the aorta, etc., and the like) is preferred, and specifically, proximal portion of the aorta is preferred. In the present case, the coronary artery (preferably, left coronary artery; more preferably, the proximal point of the left coronary artery) is preferably almost entirely constricted (occluded) by the coronary stenosis, and for example, is preferably blocked by not less than 80% of the blood vessel diameter (diameter of the blood vessel) (preferably, not less than 90% of the blood vessel diameter; more preferably, 95% to 100% of the blood vessel diameter).

On the other hand, the stenosis of the artery other than the coronary artery and the abdominal artery (e.g., thoracic aorta, ascending aorta, the proximal portion of the aorta and the like) is preferably mild, and preferably, for example, 20% to 70% of the blood vessel diameter (preferably, 30% to 60% of the blood vessel diameter; more preferably, 40% to 50% of the blood vessel diameter) is constricted.

Furthermore, both coronary stenosis and the stenosis of the artery other than the coronary artery and the abdominal artery (e.g., thoracic aorta, ascending aorta, proximal portion of the aorta and the like) are started within the same period of time, wherein the term "the same period of time" means the period wherein the model animal is still in the acute state due to the starting of the former stenosis of the artery, during the period from the starting of the stenosis of one artery to the starting of the stenosis of the other artery. That is, it means the period wherein the load to the animal is greater than those in the case wherein the period from the starting of the stenosis of one artery to the starting of the stenosis of the other artery is 2 to 3 weeks, and specifically, the period from the starting of the stenosis of one artery to the starting of the stenosis of the other artery is preferably within 1 week, specifically within 2 to 3 days, especially within 1 to 2 days. In particular, it is desirable that the coronary stenosis and the stenosis of the artery other than the coronary artery and the abdominal artery (e.g., thoracic aorta, ascending aorta, proximal portion of the aorta and the like) are started simultaneously, wherein the "simultaneously" includes some time interval (e.g., about 60 minutes to 1 minute; preferably within 30 minutes; more preferably within 5 minutes; and the like).

In the present case, although either the coronary stenosis or the stenosis of the artery other than the coronary artery and the abdominal artery may be firstly conducted, it is preferable to conduct the coronary stenosis firstly. Any means for conducting the coronary stenosis and the stenosis of the artery other than the coronary artery and the abdominal artery may be used so long as the above-mentioned blood vessel diameter is constricted, and include, for example, means such as ligature with a thread and the like, attaching a tube (the tube has a smaller diameter than that of the blood vessel) and the like, and a method comprising constricting the stenosis portion of the blood vessel together with a wire running alongside the vessel (the wire has a smaller diameter than that of the blood vessel) with a thread and the like, followed by removing the wire, and the like.

The modification such as the increase or decrease in the mortality rate after 1 week of the starting of the stenosis and the like is possible, for example, by suitably modifying the degree and stage of the above-mentioned stenosis.

The "animal model of heart failure" in the present invention has a mortality rate of not less than 20% after 1 week of starting of the stenosis of the artery (preferably not less than 30%, more preferably not less than 40%), and expresses severe cardiac dysfunction within 1 week of starting of the stenosis of the artery. Therefore, the animal model can be usefully and effectively applied to the screening of a substance to be used for prevention or treatment of heart failure (e.g., a medicament to be used for prevention or treatment heart failure and the like, such as GRK2 inhibitors and the like, and the like).

For example, the medicament to be used for prevention or treatment of heart failure can be evaluated, by investigating benefical effects of the subject substance, by administrating about 0.01 to 1000 mg/kg (preferably about 0.1 to 100 mg/kg) of the subject substance to the animal model of heart failure in the present invention and using benefical effect for cardiac dysfunction, the mortality rate and the like as an index. In the present case, the concept of preventing heart failure includes prevention of recurrence of heart failure, and the concept of treatment for heart failure includes improvement of heart failure, prevention of progression and prevention of becoming more serious. The time period for administration of the subject substance to the animal model of heart failure in the present invention includes, before starting stenosis of the artery; after starting stenosis of the artery to before cardiac dysfunction; after cardiac dysfunction; and the like, and in each administration period, the evaluation of the drug for the purpose of prevention of heart failure or treatment for slight or severe heart failure.

Furthermore, various medical substances can be evaluated by applying the subject substance to the animal model of heart failure in the present invention to investigate the life prolongation effect and the effect on heart failure (including aggravated, non-affected, improved).

In the present case, as the subject substance, known synthetic compound, peptide, protein and the like, as well as tissue extract, cell culture supernatant of warm-blooded mammal (for example, mouse, rat, swine, cattle, sheep, simian, human and the like) and the like, are used.

The subject substance, which has been determined to have benefical effects on heart failure or the medical substance, which have been determined to have effects on heart failure, by the above-mentioned screening method, can be administrated orally or parenterally as it is or in combination with a pharmacologically acceptable carrier. As a method for formulating the substance into the dosage form such as oral formulation such as tablet (including sugar-coated tablet, film-coated tablet), pill, granule, powder, capsule (including soft capsule), syrup, emulsion, suspension and the like; parenteral formulation such as injection, infusion, drop, suppository and the like; and the like, the known formulation methods that have been generally used in the art may be applied. When the substance is formulated into the above-mentioned dosage form, excipient, binder, disintegratant, lubricant, sweetening agent, surfactant, suspending agent, emulsifier and the like, which are generally used in the art of formulation, may be optionally suitably incorporated in a suitable amount during formulation of the dosage form. Furthermore, if desired, coloring agent, preservative, aromatic, flavoring agent, stabilizer, thickening agent and the like, which are generally used in the art of formulation, may be added in a suitable amount.

EXAMPLES

Hereinafter the present invention is explained in more detail with referring to the following Examples, but the present invention is not limited thereto.

Example 1

[Experiment Method]

A male JCL-Wistar rat (13 to 15 week-old) was anesthetized with pentobarbital (50 mg/kg, i.p.) and subjected to thoracotomy at the midline under artificial respiration. The pericardium was dissected to expose the heart, and the proximal portion of the ascending aorta was dissected. A thread was put through the proximal portion of the left coronary artery along with the cardiac muscle, with a needled suture, and the thread was ligated to occlude the coronary artery. Immediately after the occlusion of the coronary artery (within 5 minutes), a polyethylene tube having a length of 3 mm (outer diameter: 2.80 mm; inner diameter: 1.77 mm) was installed on the proximal portion of the ascending aorta to conduct stenosis of 40 to 50%. After that, close-chest operation was conducted, and the rat was returned to a breeding cage after spontaneous respiration had been confirmed, and bred for 1 week by a general procedure. The rats in which the recovery of spontaneous respiration had not been confirmed were excluded from the following analysis. After 1 week of the operation, to measure the hemodynamics, the rat was anesthetized with pentobarbital (40 mg/kg, i.p.). A tracheal cannula was inserted, then a mirror catheter having a pressure sensor (2F) was inserted from the right carotid artery to the left ventricle. The waveform of the left ventricular pressure was analyzed with a differential amplifier, and the maximum differential value (LVdp/dt$_{max}$) and the minimum differential value (LVdp/dt$_{min}$) were recorded.

On the other hand, in order to measure the blood pressure and to administrate a drug, a polyethylene tube was inserted to the left femoral artery and left femoral vein, respectively, and the heart rate carculated from the blood pressure pulse and the dipolar lead (II) electrocardiogram were recorded.

Dobutamime was dissolved in a solution of saline containing 0.01% of ascorbic acid, and the solution was administrated in a dose of 0.3 to 10 μg/kg i.v. to investigate the β-receptor response.

The basal hemodynamics after 1 week of the operation was represented by the value before the administration of dobutamime, and the reactivity of the β-receptor was represented by the difference between before and after the administration of dobutamime (Δ mmHg/sec) by the mean value±standard error.

[Results]

(1) Mortality Rate

For the group in which the coronary stenosis and the stenosis of the proximal portion of the aorta had been conducted (n=14), 10 of 14 rats died within 1 week, and the mortality rate was 71% (one died on the third day, two died on the fourth day, three died on the fifth day, and four died on the sixth day, respectively). The living four rats were used for the following analyses.

On the other hand, none of the rats died within 1 week, for the sham-operated group (n=2), the group in which the coronary stenosis had been conducted (n=3) and the group in which the stenosis of the proximal portion of the aorta had been conducted (n=2).

(2) Hemodynamics 1 Week after the Operation

For the group in which the coronary stenosis and the stenosis of the proximal portion of the aorta have been conducted, LVdp/dt$_{max}$ and LVdp/dt$_{min}$ were 7777 mmHg/sec and −6145 mmHg/sec respectively, which were significantly low as compared with those of the sham-operated group (LVdp/dt$_{max}$: 12841 mmHg/sec; LVdp/dt$_{min}$: −11121 mmHg/sec).

For the group in which the coronary stenosis and the stenosis of the proximal portion of the aorta have been conducted, the left ventricle end-diastolic pressure (LVEDP) was increased by 18.1 mmHg, which was significantly high as compared with that of the sham-operated group (2.4 mmHg).

For the group in which the coronary stenosis and the stenosis of the proximal portion of the aorta have been conducted, the blood pressure and heart rate did not show the significant changes as compared with those of the sham-operated group.

(3) Effect on the Heart Weight

The weight of the left ventricle per the body weight for the group in which the coronary stenosis and the stenosis of the proximal portion of the aorta had been conducted was 215 mg/100 g, whereas that of the sham-operated group was 186 mg/100 g, and the weight of the right ventricle per the body weight for the group in which the coronary stenosis and the stenosis of the proximal portion of the aorta had been conducted was 65 mg/100 g, whereas that of the sham-operated group was 45 mg/100 g, confirming the cardiac hypertrophy.

(4) Reactivity for Dobutamime

For all of the administration dose of dobutamime of 0.3, 1.0, 3.0, 10 µg/kg, i.v., the group in which the coronary stenosis and the stenosis of the proximal portion of the aorta had been conducted remarkably decreased the maximum reaction of $LVdp/dt_{max}$, as compared with that of the sham-operated group. The results are shown in Table 1.

TABLE 1

| | The group in which the coronary stenosis and the stenosis of the proximal portion of the aorta had been conducted (Δ mmHg/sec) | Sham-operated group (Δ mmHg/sec) |
|---|---|---|
| Dobutamine 0.3 µg/kg, i.v. | 278 ± 144 | 2287 ± 8 |
| Dobutamine 1.0 µg/kg, i.v. | 832 ± 501 | 4127 ± 112 |
| Dobutamine 3.0 µg/kg, i.v. | 1641 ± 794 | 7135 ± 753 |
| Dobutamine 10 µg/kg, i.v. | 2431 ± 1028 | 7654 ± 999 |

INDUSTRIAL APPLICABILITY

The animal model of heart failure in the present invention is superior as an in vivo evaluation system, since it expresses the pathology of terminal heart failure in a short period, and which can be usefully and effectively applied to the screening of a substance to be used for prevention or treatment of heart failure. Furthermore, the animal model is useful as an evaluation system, which determines whether the substance to be used for prevention or treatment of the diseases other than heart failure aggravates the pathology of heart failure or not. Furthermore, by using the heart failure model of the present invention, various studies on the pathologic physiology aiming at explication of the pathologic mechanism of heart failure, such as the identification of the gene in which the expression thereof varies depending on pathology and its change in the expression level, the analysis of variation in the protein expression, the investigation for the benefical effect on heart failure by transgene, and the like, can be effectively conducted in a short period.

The invention claimed is:

1. A method for preparing a non-human mammalian model of heart failure which comprises starting both coronary artery stenosis and the stenosis of the thoracic aorta in said non-human mammal within the same period of time, wherein said period of time is that after the starting of one stenosis, the other is started while the mammal is still in an acute state due to the former stenosis, wherein the second stenosis is performed within one week.

2. The method according to claim 1, wherein the non-human mammal is a rabbit, a dog, a cat, a guinea pig, a hamster, a mouse or a rat.

3. The method according to claim 1, wherein the non-human mammal is a rat.

4. The method according to claim 1, wherein the heart failure is due to a decrease of cardiac contractility.

5. The method according to claim 1, wherein the heart failure is due to an increase in the left ventricular end-diastolic pressure.

6. The method according to claim 1, wherein the heart failure is cardiac hypertrophy.

7. The method according to claim 1, wherein the heart failure is due to a decrease in reactivity to catecholamine.

8. The method according to claim 1, wherein the coronary artery stenosis is the blocking of not less than 80% of the blood vessel diameter of the coronary artery.

9. The method according to claim 1, wherein the stenosis of the thoracic aorta is the blocking of 20% to 70% of the diameter of the blood vessel in the artery.

10. The method according to claim 1, wherein, after the starting of one stenosis, the other stenosis is started within 1 or 2 days.

11. The method according to claim 1, wherein, after the starting of one stenosis, the other stenosis is started within 60 minutes.

12. The method according to claim 1, wherein, after the starting of one stenosis, the other stenosis is started within 5 minutes.

13. The method according to claim 1, wherein the coronary artery stenosis and the stenosis of the thoracic aorta are simultaneously started.

14. The method according to claim 1, wherein the coronary artery stenosis is started prior to the starting of the stenosis of the thoracic aorta.

15. The method according to claim 1, wherein the survival rate of the non-human mammalian model of heart failure is not less than 90% after 2 hours of the starting of the stenosis, and the mortality rate of the non-human mammalian model of heart failure is not less than 20% after 1 week of the starting of the stenosis.

16. The method according to claim 15, wherein the mortality rate is not less than 50% after 1 week of the starting of the stenosis.

17. A method for screening a medical substance which comprises applying a subject substance to the non-human mammalian model of heart failure according to claim 1, and assaying the effect of the substance on heart failure.

18. The method according to claim 17, wherein the medical substance is a substance to be used for prevention or treatment of heart failure.

* * * * *